US012253517B2

(12) United States Patent
Baier et al.

(10) Patent No.: US 12,253,517 B2
(45) Date of Patent: Mar. 18, 2025

(54) NANO-ENZYME CONTAINERS FOR TEST ELEMENTS

(71) Applicant: Roche Diabetes Care, Inc., Indianapolis, IN (US)

(72) Inventors: Grit Baier, Illertissen (DE); Carina Horn, Biblis (DE); Katharina Landfester, Mainz (DE); Anna Musyanovych, Mainz (DE); Umaporn Paiphansiri, Ludwigshafen (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 648 days.

(21) Appl. No.: 17/407,283

(22) Filed: Aug. 20, 2021

(65) Prior Publication Data

US 2021/0382042 A1 Dec. 9, 2021

Related U.S. Application Data

(60) Division of application No. 15/141,062, filed on Apr. 28, 2016, now Pat. No. 11,105,800, which is a continuation of application No. PCT/EP2014/072994, filed on Oct. 27, 2014.

(30) Foreign Application Priority Data

Oct. 29, 2013 (EP) ..................................... 13190709

(51) Int. Cl.

| G01N 33/543 | (2006.01) |
| C08G 18/28 | (2006.01) |
| C12N 9/04 | (2006.01) |
| C12N 11/093 | (2020.01) |
| C12N 11/098 | (2020.01) |
| C12Q 1/00 | (2006.01) |
| C12Q 1/32 | (2006.01) |
| C12Q 1/54 | (2006.01) |
| G01N 33/487 | (2006.01) |
| G01N 33/50 | (2006.01) |

(52) U.S. Cl.
CPC ....... *G01N 33/5432* (2013.01); *C08G 18/289* (2013.01); *C12N 9/0006* (2013.01); *C12N 11/093* (2020.01); *C12N 11/098* (2020.01); *C12Q 1/006* (2013.01); *C12Q 1/32* (2013.01); *C12Q 1/54* (2013.01); *G01N 33/48721* (2013.01); *G01N 33/5038* (2013.01); *G01N 33/54346* (2013.01)

(58) Field of Classification Search
CPC ......... G01N 33/5432; G01N 33/54346; C08G 18/289; C12N 11/00; C12N 11/02; C12N 11/04; C12N 11/14
See application file for complete search history.

(56) References Cited

U.S. PATENT DOCUMENTS

| 6,495,352 B1 | 12/2002 | Brinker et al. |
| 2007/0026476 A1 | 2/2007 | Heindl et al. |
| 2008/0220460 A1 | 9/2008 | Kawaminami et al. |
| 2010/0184121 A1 | 7/2010 | Misiak et al. |
| 2011/0186428 A1 | 8/2011 | Beaty et al. |
| 2014/0186436 A1 | 7/2014 | Yang et al. |

FOREIGN PATENT DOCUMENTS

| DE | 197 53 847 A1 | 12/1997 |
| EP | 0 821 233 A2 | 1/1998 |
| EP | 1 035 921 A1 | 9/2000 |
| EP | 0 821 234 B1 | 10/2002 |
| EP | 1 593 434 A2 | 11/2005 |
| EP | 2 084 292 B1 | 2/2011 |
| WO | WO 2006/040172 A1 | 4/2006 |
| WO | WO 2007/012494 A1 | 2/2007 |
| WO | WO 2009/029180 A1 | 3/2009 |
| WO | WO 2009/103540 A1 | 8/2009 |
| WO | WO 2010/097619 A1 | 9/2010 |
| WO | WO 2013/006763 A1 | 1/2013 |

OTHER PUBLICATIONS

Ammam et al., Sensors and Actuators 8 155 (2011) 340-346 (Year: 2011).
Berti, Francesca et al., "New Micro- and nanotechnologies for Electrochemical Biosensor Development", Biosensor Nanomaterials, Mar. 19, 2011 (Mar. 19, 2011), XP002721488, Retrieved from the Internet: URL:http://www.wiley-vch.de/books/sample/3527328416_c01.pdf [retrieved on Mar. 11, 2014].
Cao at al. "Preparation of mesoporous submicrometer silica capsules via an interfacial Sol-Gel process in inverse miniemulsion", Langmuler, 2012, vol. 28, pp. 7023-7032.
Cellesi et al. 'Sol-gel synthesis at neutral pH in W/O microemulsion: A method for enzyme nanoencapsulation in silica gel nanoparticles', Colloids and Surfaces A: Physicochemical and Engineering Aspects, vol. 288, Issues 1-3, Oct. 5, 2006, pp. 52-61.
English Abstract of DE 197 53 847 A1 Dec. 4, 1997 obtained from Lexis Nexis Total Patent on Jul. 28, 2017.
English Abstract of EP 0 821 233 A2 Jan. 28, 1998 obtained from Lexis Nexis Total Patent on Jul. 28, 2017.
English Abstract of EP 0 821 234 B1 Oct. 9, 2002 obtained from Lexis-Nexis Total Patent on Jul. 28, 2017.
English Abstract of EP 2 084 292 B1 obtained from Lexis-Nexis Total Patent on Jul. 28, 2017.
Englsih Abstract of EP 1 593 434 A2 Nov. 9, 2005 obtained from Lexis-Nexis Total Patent on Jul. 28, 2017.
Hoenes et al. "The technology behind glucose meters: Test strips", Diabetes Technology& Therapeutics, 2008, vol. 10, Suppl. 1, S13.
International Preliminary Report on Patentability for PCT/EP2014/072994 Issued May 3, 2016.
Kothamasu et al., 'Nanocapsules: the weapons for novel drug delivery systems', BioImpacts, 2012:2(2):71-81. [online] [retrieved on Sep. 13, 2018]. Retrieved from the Interned: < URL: https://bi.tbzmed.ac.ir/Article/BI_72_20110824114921>.

(Continued)

*Primary Examiner* — Ruth A Davis
(74) *Attorney, Agent, or Firm* — Woodard, Emhardt, Henry, Reeves & Wagner, LLP

(57) ABSTRACT

The present invention relates to a test element for the detection of an analyte comprising an enzyme, wherein the enzyme is incorporated in a nanocapsule.

12 Claims, 19 Drawing Sheets

(56) References Cited

OTHER PUBLICATIONS

Li et al. "A novel amperometric biosensor based on NiO hollow nanospheres for biosensing glucose". Talanta, 2008, vol. 77, pp. 455-459.

Montalvo-Ortiz et al. "Improved enzyme activity and stability in polymer microspheres by encapsulation of protein nanospheres", AAPS PharmSciTech, 2012, vol. 13, pp. 632-636.

Mureseanu et al., 'A New Mesoporous Micelle-Templated Silica Route for Enzyme Encapsulation', Langmuir, 2005. 21 (10), pp. 4648-4655 DOI: 10.1021/la0502241, Publication Date (Web): Mar. 23, 2005.

Park et al. "Fabrication of hollow silica microspheres through the self-asssembly behavior of polymers in W/O emulsion", Chemisty Letters, 2003, vol. 32, No. 7, pp. 598-599.

Price et al., 'A rapid kinetic assay for glucose using blucose dehydrogenase', Annals of Clinical Biochemistry, 1979, 16, 100-105, [online] [retrieved on Sep. 13, 2018]. Retrieved from the Internet: < URL: https://journals.sagepub.com/doi/pdf/10.1177/000456327901600120>.

Radol, A., et al., "Detection of NADH via electrocatalytic oxidation at single-walled carbon nanotubes modified with Variamine blue", Electrochimica Acta, Jan. 1, 2008 (Jan. 1, 2008) pp. 2161-2169. XP002721489.

Rahman, Mahbubur, MD, et al., "A Comprehensive Review of Glucose Biosensors Based on Nanostructured Metal-Oxides", Sensors 2010, vol. 10, No. 5, pp. 4855-4886, XP002721487, ISSN: 1424-8220.

Sinha, Sujata et al., "NAD (H) Linked Enzyme Catalyzed Reactions uisng Coupled Enzymes in a Composite Nanoparticle System", Enzyme Engineering 2013, vol. 2, Issue 2.

Yudkin, John "The dehydrogenases o *Bacterium coli*, II. The rate of reduction of methylene blue". Biochem. J., 28, 1934, 1454-1462.

A

B

C

NANO-ENZYME CONTAINERS FOR TEST ELEMENTS

The present invention relates to a test element for the detection of an analyte comprising an enzyme, wherein the enzyme is incorporated in a nanocapsule. Further, the invention relates to a method of producing a nanocapsule having incorporated therein an enzyme molecule.

The utility of enzymes as 'biological reporters' offers considerable promise for many biomedical applications, e.g. glucose biosensors. Due to the increased demand of self blood glucose monitoring, the development of rapid and accurate test devices using sub-microliters blood volume has been highly focused, since Clark and Lyons first proposed enzyme electrodes in 1962. Besides purposely tailoring the enzyme molecules, for instance glucose dehydrogenase (GDH) in order to increase its glucose specificity and its activity, the preparation methods significantly affect the reliability of the sensor.

In order to obtain reliable test results, various approaches for immobilizing enzymes on test elements are known in the art. WO 2009/029180 describes the loadings of enzymes in nano fibres. This method, however, requires solubilisation of the enzyme to be encapsulated in an organic solvent which may have a detrimental effect on enzyme activity and/or stability.

WO 2010/097619 describes immobilisation of enzymes and coenzymes in controlled pore glass particles. These particles, however, have an average diameter of about >40 μm and, thus, are difficult to incorporate into test elements.

The application of hollow silica microspheres through the self-assembly behaviour of polymers in a water-in-oil-emulsion is described by Park et al. (Chemistry Letters 32 (2003), 598-599). The resulting particles have a size of >1 μm and a high shell-wall thickness in the range of 100-400 nm. The particle cores contain hydrophilic polymers such as polyvinylpyrrolidone or polyethylene glycol.

Cao et al. (Langmuier 28 (2012), 7023-7032) describes preparation of mesoporous submicrometer silica capsules via an interfacial sol-gel process in an inverse miniemulsion. The silica shell of the capsule is formed by a condensation reaction of tetraethoxysilane (TEOS) on the surface of aqueous droplets in an oil phase. The aqueous phase contains cetyltrimethylammonium bromide (CTAB) as a structuring surfactant. In the absence of CTAB only solid silica particles without core are formed. The presence of hydrophilic polymers and/or structuring surfactants in the core might negatively affect stability and/or activity of encapsulated enzymes.

Thus, there is a need to provide capsules comprising active enzyme molecules incorporated therein, which are suitable for incorporation in test elements.

In the present application, it is reported for the first time a single-step preparation procedure of well-defined aqueous core shell nanocapsules, the core of which contains an active enzyme, e.g. a nicotinamide adenine dinucleotide ($NAD^+$/NADH) dependent GDH, by an inverse miniemulsion process and without the presence of any structuring surfactants in the aqueous phase. The process also avoids the use of an additional acidic or basic catalyst which might affect enzyme activity and/or stability.

In one embodiment, our concept involves the use of (poly)isocyanate and (poly)hydroxy or amino precursors that are added to a water-in-oil-emulsion. As soon as the isocyanate precursors present in the oil phase come into contact with the aqueous droplets comprising the enzyme to be encapsulated, e.g. GDH, and the hydroxy or amino precursors, a polyaddition reaction takes place resulting in the formation of poly(urethane/urea) shells containing encapsulated enzyme molecules in active form.

In a further embodiment, our concept involves the use of mixed silica precursors such as an alkyltrichlorosilane and a tetraalkoxysilane that are added to a water-in-oil-emulsion. As soon as the precursors reach the aqueous droplets comprising the enzyme to be encapsulated, e.g. GDH, a hydrolysis and co-condensation reactions take place resulting in the formation of silica shells containing encapsulated enzyme molecules in active form.

Thus, in one aspect, the present invention relates a nanocapsule having incorporated therein an enzyme. The nanocapsule is substantially impermeable for the encapsulated enzyme, but permeable for an enzyme substrate. Further, the interior of the nanocapsule may comprise a coenzyme such as $NAD^+$/NADH or $NADP^+$/NADPH. Preferably, the interior of the nanocapsule is free from a structuring surfactant, particularly CTAB, and/or from a hydrophilic polymer, particularly polyethylene glycol and/or polyvinylpyrrolidone.

The nanocapsule may be formed by a polyaddition and/or condensation of monomers in a water-in-oil-miniemulsion comprising a continuous oil phase and a discontinuous aqueous phase dispersed therein, wherein the enzyme is present in the aqueous phase. Preferably, the aqueous phase does not contain a structuring surfactant, particularly CTAB, and/or a hydrophilic polymer, particularly polyethylene glycol and/or polyvinylpyrrolidone.

In a further aspect, the present invention relates to a method of manufacturing a nanocapsule having incorporated therein an enzyme comprising a polyaddition and/or polycondensation of monomers in a water-in-oil-miniemulsion comprising a continuous oil phase and a discontinuous aqueous phase dispersed therein, wherein the enzyme is present in the aqueous phase, and wherein a nanocapsule comprising a shell having the enzyme encapsulated therein is obtained. The method may further comprise removal of the outer oil phase and the volatile constituents of the inner aqueous phase thereby obtaining a dry nanocapsule. The dry nanocapsule may be rehydrated thereby retaining the enzymatic activity of the encapsulated enzyme.

In a further aspect, the present invention relates to a diagnostic test element for the detection of an analyte comprising an enzyme, wherein the enzyme is incorporated in a nanocapsule.

The test element or the nanocapsule are suitable for use in a method for detecting an analyte in a sample by an enzymatic reaction, e.g. for diagnostic applications.

In still a further aspect, the present invention relates to a method for determining an analyte by an enzymatic reaction, comprising the steps: (a) providing a sample suspected to contain the analyte, (b) contacting the sample with a nanocapsule having incorporated therein an enzyme capable of an enzymatic reaction which allows detection of the analyte, wherein the nanocapsule is impermeable for the enzyme, but permeable for an enzyme substrate, and (c) detecting an enzymatic reaction between enzyme and enzyme substrate, and thereby determining the presence and/or amount of analyte in the sample.

According to the present invention, nanocapsules having incorporated therein an enzyme molecule are provided. The nanocapsules preferably have an average diameter of 1 μm or less, e.g. from about 50 nm to about 500 nm, and particularly of from about 100 nm to about 350 nm as measured by dynamic light scattering. Preferably, the nanocapsules have an average shell thickness from about 3 to about 100 nm, more preferably from about 5 to about 50 nm and even more preferably from about 7 to about 14 nm. The nanocapsules should be impermeable for the encapsulated enzyme, but permeable for an enzyme substrate. Thus, the nanocapsule may have pores with a maximum size which is smaller than the size of the enzyme and wherein the average pore size may be <100 nm, preferably from about 1 to about 15 nm and even more preferably from about 1 to about 3 nm or from about 5 to about 15 nm.

The enzyme incorporated in the nanocapsule is preferably a coenzyme-dependent enzyme. Suitable enzymes are e.g. dehydrogenases selected from the group consisting of a glucose dehydrogenase, GDH (e.g. a NAD(P)-dependent glucose dehydrogenase (EC 1.1.1.47), a FAD-dependent glucose dehydrogenase (E.C. 1.1.1.99.10) or a PQQ-dependent glucose dehydrogenase (E.C. 1.1.5.2), glucose-6-phosphate dehydrogenase (EC 1.1.1.49), lactate dehydrogenase (EC 1.1.1.27; EC 1.1.1.28), malate dehydrogenase (EC 1.1.1.37), glycerol dehydrogenase (EC 1.1.1.6), alcohol dehydrogenase (EC 1.1.1.1; EC 1.1.1.2), α-hydroxy butyrate dehydrogenase (EC 1.1.1.30), sorbitol dehydrogenase or an amino acid dehydrogenase such as an L-amino acid dehydrogenase (EC 1.4.1.5). Further suitable enzymes are oxidases such as glucose oxidase (EC 1.1.1.34) or cholesterol oxidase (EC 1.1.1.36) or amino transferases such as aspartate or alanine amino transferase, 5'-nucleotidase or creatin kinase or diaphorase (EC 1.6.99.2). Preferably, the enzyme is a NAD(P)-dependent GDH including mutants, e.g. as described in WO 2009/103540, incorporated herein by reference, a FAD-dependent GDH including mutants, e.g. as described in US 2008/0220460, incorporated herein by reference, or a PQQ-dependent GDH including mutants, e.g. as described in WO 2006/040172, incorporated herein by reference.

In some embodiments, the interior of the nanocapsule also comprises a coenzyme of the encapsulated enzyme. Preferred examples of coenzymes are nicotine amide adenine dinucleotide (NAD or NADH) or nicotine amide adenine dinucleotide phosphate (NADP or NADPH), or derivatives thereof, including stabilized derivatives as disclosed in WO 2007/012494, or U.S. Ser. No. 11/460,366, or WO 2009/103540, the contents of which are herein incorporated by reference. Especially preferred is carba-NAD, carba-NADPH, carba-NADP or carba-NADPH. Further preferred examples of coenzymes are flavin adenine (FAD or $FADH_2$), flavin mononucleotide (FMN) or pyrroloquinoline quinone (PQQ).

In some embodiments, the enzyme is a NAD(P)-dependent GDH, a FAD-dependent GDH or a PQQ-dependent GDH which may be encapsulated together with the respective coenzyme.

In other embodiments, the interior of the nanocapsule also comprises an electron acceptor for the enzyme, e.g. oxygen, a mediator or a redox dye as a primary electron acceptor.

In some embodiments, the enzyme is an oxidase, e.g. a glucose oxidase which may be encapsulated with a primary electron acceptor thereof, e.g. oxygen, a mediator or a redox dye, e.g. as described in Hoenes et al., Diabetes Technology & Therapeutics 10 Suppl. 1 (2008), p. S13, incorporated herein by reference.

A diagnostic test element comprising an enzyme incorporated in a nanocapsule as described above may be any test element which is known to the skilled person in the field of diagnostic, e.g. a photometric or amperometric test element. Preferably, the test element may be a test band, test disc, test pad or test strip as known in the art, such as a photometric capillary test strip, e.g. as described in EP 1 035 921 B1, a photometric test band, e.g. as described in EP 1 593 434 A2, a photometric top-dosing test strip as described in EP 0 821 233 B1 or EP 0 821 234 B1, or an amperometric capillary test strip, e.g. as described in EP 2 084 292 B1 or US 2011/0186428 A1, the contents of which are herein incorporated by reference. In a preferred embodiment, the test element comprises the enzyme-containing nanocapsule in a dry state, wherein the content of the interior of the capsule is present in a dry, e.g. freeze-dried or lyophilized form. In addition to the enzyme and optionally the coenzyme, the capsule interior may comprise further compounds such as buffer substances, etc.

Preferably, the interior of the nanocapsule is free from a structuring surfactant, such as CTAB, and/or a hydrophilic polymer such as polyethylene glycol, polyvinylpyrrolidone or a polycaccharide, e.g. a dextran and/or organic solvents, such as acetone, cyclohexane, and/or crosslinkers, such as diisocyanates (e.g. TDI). The capsule walls may, however, have stabilizing groups covalently attached thereto, e.g. polar and/or charged groups such as —OH, —N(R')$_3$, wherein R' is $C_{1-3}$ alkyl, —$SO_3^{2-}$, guandinium etc. The polar and/or charged groups may be present as substituents on $C_{1-12}$, particularly $C_{3-8}$ groups.

The test element comprises at least one layer comprising the nanocapsules including the enzyme and optionally further layers, e.g. cover or coating layers as known in the art. The layers may have a thickness from about 1 to about 200 µm, preferably from about 2 to about 100 µm or from about 3 µm to about 50 µm. Preferably, the test element is free from non-encapsulated enzyme.

The test element is suitable for the detection of any biological or chemical substance which is detectable by an enzymatic reaction, i.e. an enzymatic reaction catalysed by the nanoencapsulated enzyme. Suitable analytes are e.g. alcohol, ammonium, ascorbic acid, cholesterol, cysteine, glucose, glutathion, glycerol, 3-hydroxybutyrate, lactic acid, pyruvate, salicylate, tri-glycerides, malic acid or urea. Preferably, the analyte is glucose.

The test element is suitable for detecting analytes present in a sample, particularly in a liquid sample such as a body fluid sample, such as whole blood, plasma, serum, extracellular tissue fluid, lymphatic fluid, cerebrospinal fluid, urine, saliva or sweat. Preferably, the diagnostic test element is suitable for detecting the presence and/or amount of an analyte as indicated above in a sample selected from whole blood, plasma, serum, or extracellular tissue fluid.

The detection of the analyte may be a qualitative and/or quantitative detection according to known enzymatic detection methods, wherein a detectable signal is generated by an enzymatic reaction which can be read out according to suitable techniques, e.g. optical methods such as absorption, fluorescence, circular dichroism, optical rotation dispersion, refractrometry, etc. or by electrochemical techniques.

Preferably the test element is a glucose sensor comprising a nanocapsule having incorporated therein an enzyme suitable for the detection of glucose such as a coenzyme-dependent glucose dehydrogenase or a coenzyme-dependent glucose-6-phosphate dehydrogenase or a glucose oxidase. The enzyme is encapsulated together with suitable buffer substances in order to provide a pH at which the enzyme is active and stable. For glucose dehydrogenase, buffer substances in order to adjust a pH of about 7.5 to 9.0, e.g. about 8.5, are preferred.

The encapsulated enzyme retains its activity after drying, e.g. by freeze-drying or lyophilisation and subsequent rehydratation. The specific activity of encapsulated glucose dehydrogenase is preferably about 15 U/mg to 50 KU/mg, e.g. 15 U/mg to 500 U/mg or 500 U/mg to 50 KU/mg, based on the amount of encapsulated enzyme.

The present invention also refers to a method for manufacturing a nanocapsule having incorporated therein an enzyme. This method preferably comprises a polyaddition and/or polycondensation of suitable monomers in a water-in-oil-miniemulsion comprising a continuous oil phase and a discontinuous aqueous phase dispersed in the continuous oil phase, wherein the enzyme is present in the dispersed aqueous phase. Preferably, the average size of the aqueous droplets is from about 50 to about 1000 nm, preferably from about 80 to about 500 nm. The nanocapsules are formed by polyaddition and/or polycondensation of the monomers at the interface of the continuous oil phase and the discontinuous aqueous phase dispersed therein. In some embodiments, all of the monomers required for nanocapsule formation, are present in the oil phase, e.g. in the manufacture silica nanocapsules. In other embodiments, one type of monomer is present in the oil phase and the other monomer is present in the aqueous phase, e.g. in the manufacture of poly (urethane/urea) nanocapsules.

The oil phase may be formed from a water-immiscible organic solvent, e.g. a hydrocarbon such as cyclohexane, hexane, heptane, toluene, light mineral oil, etc. In some embodiments, the oil phase additionally comprises a lipophilic surfactant such as polyglycerol polyricinoleate (PGPR) or a sorbitan fatty acid ester, e.g. sorbitan monooleate (Span80) or a (polyethylene-co-butylene)-co-poly(ethylene oxide).

In a preferred embodiment, the nanocapsule is a poly (urethane/urea) capsule comprising a shell which is the reaction product of a (poly)isocyanate and an isocyanate-reactive compound, e.g. a (poly)hydroxy or amino compound. The capsule is obtainable by polyaddition of a (poly)isocyanate with an isocyanate-reactive compound at the interface of a water-in-oil-miniemulsion. As a (poly) isocyanate, a compound comprising two or more isocyanate groups, such as toluene 2,4-diisocyanate, 1,4-cyclohexyl diisocyanate, isophoron diisocyanate or hexamethylene diisocyanate is suitable. The (poly)isocyanate compound is a compound which is soluble in the oil phase.

The isocyanate-reactive compound is a hydrophilic compound soluble in the aqueous phase which comprises at least two isocyanate-reactive groups, e.g. at least two hydroxy and/or primary amino groups reactive with an isocyanate group for forming a urethane or urea group. Suitable hydroxy/amino compounds are e.g. polyalcohols, such as 1,6-hexanediol, 1,3-dihydroxyacetone, glycerol, poly(vinyl-alcohol), hydroxycarboxylic acids such as lactic acid, saccharides or glycosaminoglycans such as hyaluronic acid, di- or poly(amines) such as 1,6-diaminohexane or chitosan and combinations thereof.

Further suitable polymer shells are poly(acryalate)polymers, e.g. poly(butyl-cyanoacrylate), or poly(thio urethane/urea) polymers.

The molar ratio of isocyanate to the isocyanate-reactive compound is preferably adjusted to at least about 1:1, e.g. in the range of about 1:1 to about 1:2, preferably in the range of about 1:1 to about 1:1.5. Reaction between the monomers occurs at the interface of the oil and water phase, e.g. when the isocyanate present in the oil phase comes into contact with a hydrophilic isocyanate-reactive compound present in the aqueous phase.

In a further preferred embodiment, the nanocapsule is a silica nanocapsule. Such silica nanocapsules may be obtained by polycondensation of a tri- or tetra-alkoxysilane with a functionalized silane. As a tri- or tetraalkoxysilane, a tetra-$C_1$-$C_6$ alkoxysilane may be used such as tetraethoxysilane (TEOS) or tetramethoxysilane or a tri-$C_1$-$C_6$ alkoxyalkylsilane such as ethyltriethoxysilane. As functionalized silanes compounds $RSiX_3$ or $R_2SiX_2$ may be used, wherein X is $OCH_3$, $OCH_2CH_3$ or halo, particularly chloro, and R is an optionally substituted $C_3$-$C_{30}$, preferably $C_6$-$C_{20}$ alkyl group. The substituents of R may e.g. be selected from polar and/or charged groups such as OH, $N(R)_{3^+}$, wherein R' is $C_{1-3}$ alkyl, —$SO_3^{2-}$, guanidium etc. Preferred examples are trihaloalkylsilanes or dihalodialkylsilanes such as octadecyl-trichlorosilane (OTS), hexyltrichlorosilane (HTS), dodecyl-trichlorosilane (DTS) or combinations thereof.

The molar ratio between tri- or tetraalkoxysilane and functionalized silane is preferably in the range of about 1:1 to about 5:1, preferably from about 1.5:1 to about 3:1.

Use of an encapsulated enzyme on a diagnostic test element may improve the performance of analyte detection, e.g. detection of glucose. By encapsulation, the enzyme is immobilized whereby the enzymatic reaction with the analyte may only occur at a predetermined position on the test element. Encapsulation of the enzyme also precludes the generation of "enzyme dust", thereby avoiding contamination of test devices and reducing health risks for patients. Further, encapsulation leads to an improvement of a functional stabilization, since the enzyme—even after longer storage time—remains at a predetermined position on the test element. By immobilizing within a capsule, the enzyme activity may also be stabilized against degradation, particularly under warm and/or humid storage conditions.

In the following the present invention shall be explained in more detail by Figures and Examples.

A permeable polymeric shell (10), e.g. a poly(urethane/urea) shell or a silica shell, encapsulates a core medium (12), e.g. an aqueous buffered solution comprising an enzyme molecule (14), e.g. glucose dehydrogenase, and optionally a co-enzyme, e.g. NAD, or carba NAD (18). The polymeric shell (10) is permeable to enzyme substrate molecules (16), e.g. glucose.

FIGS. 2A-F: Scanning election microscope (SEM) images of nanocapsules prepared from 2-4-toluene diisocyanate (TDI) using different hydrophilic monomers: A: 1,6-hexanediol; B: lactic acid; C: 1,3-dihydroxyacetone; D: glycerol; E: poly(vinyl alcohol); F: hyaluronic acid.

Figure 3A:
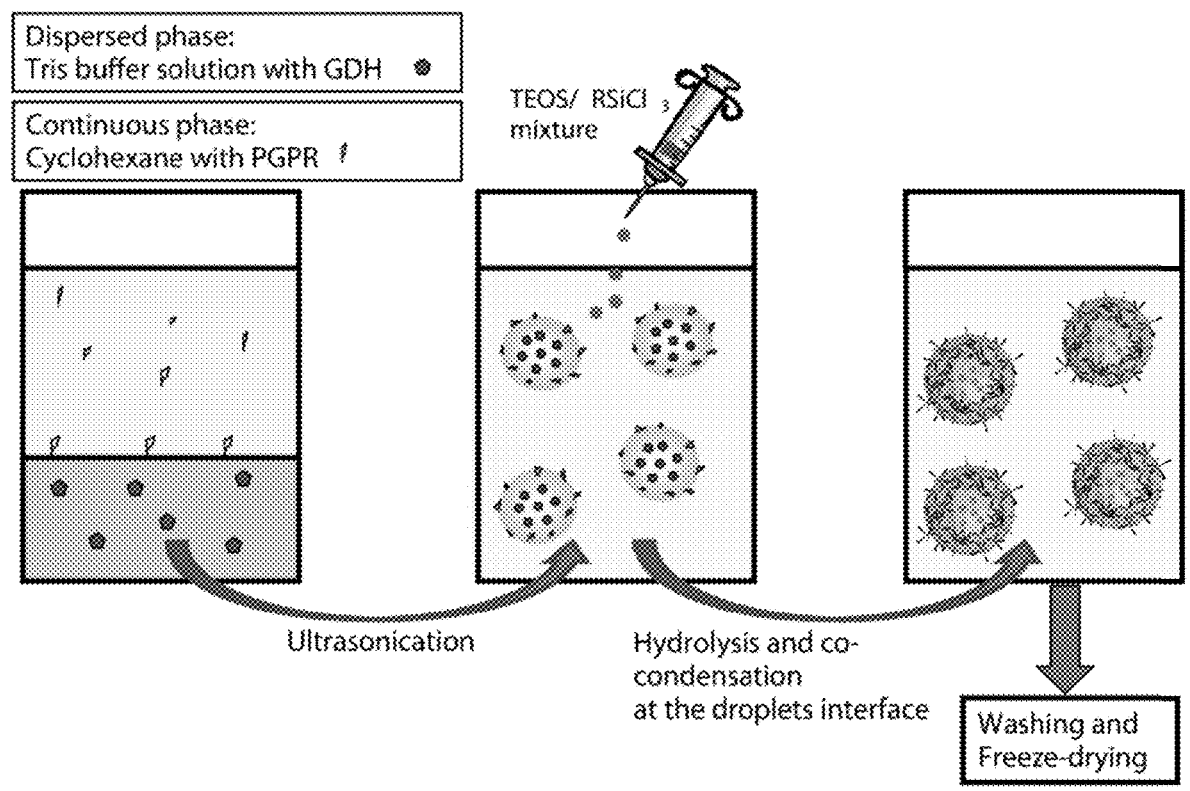
Figure 3B:
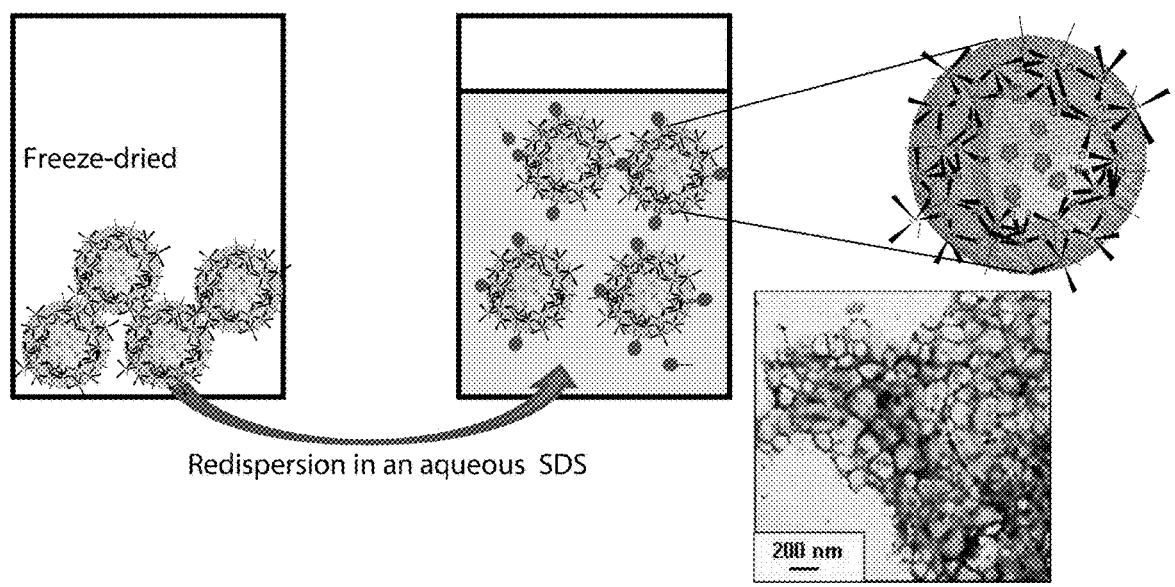
Figure 3C:
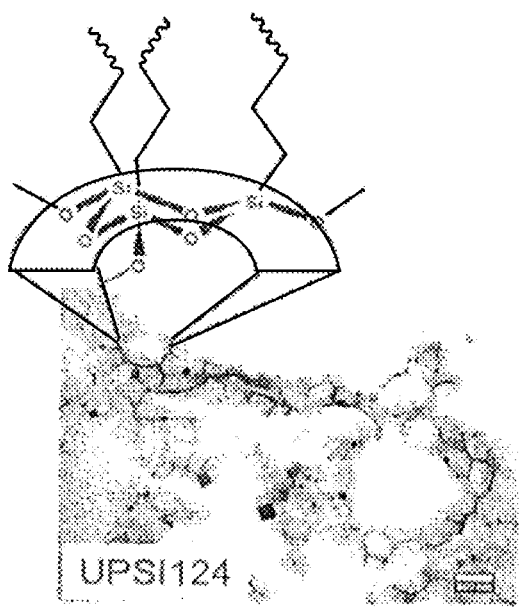

FIGS. 3A-C: Synthesis and redispersion of GDH containing silica nanocapsules:
  A) Synthesis of nanocapsules in an inverse miniemulsion.
  B) Redispersion of nanocapsules in aqueous phase.
  C) SEM image of nanocapsules including a schematic depiction of shell structure.

FIGS. 4A-E: SEM images (obtained from cyclohexane phase) represent core-shell morphology of the silica nanocapsules (sample UPSI178).

Figure 5:
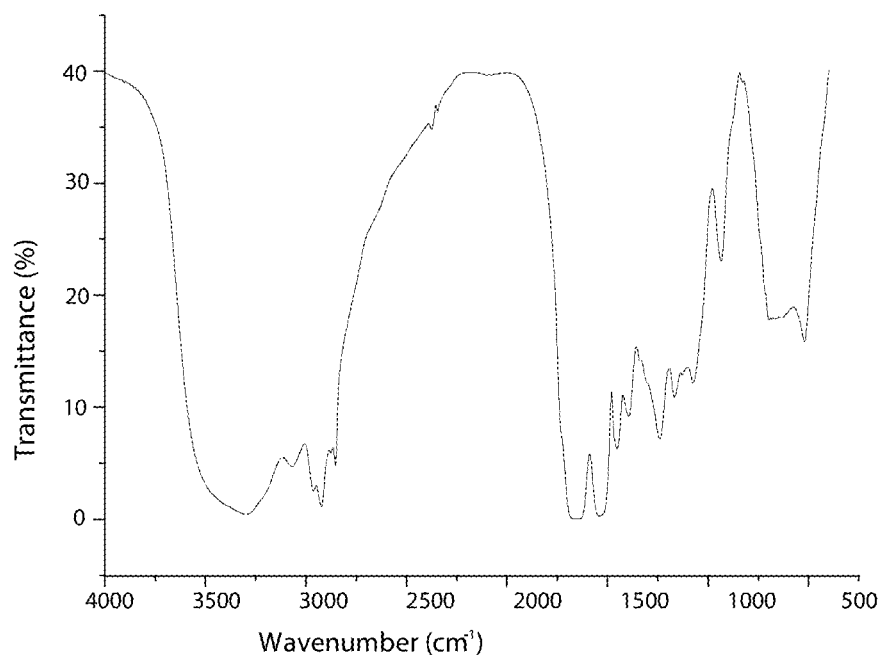

FIG. 5: FTIR spectrum of lyophilised silica nanocapsules (UPSI178) with a molar ratio of OTS:TEOS (1:1.9) in cyclohexane phase.

Figure 6:
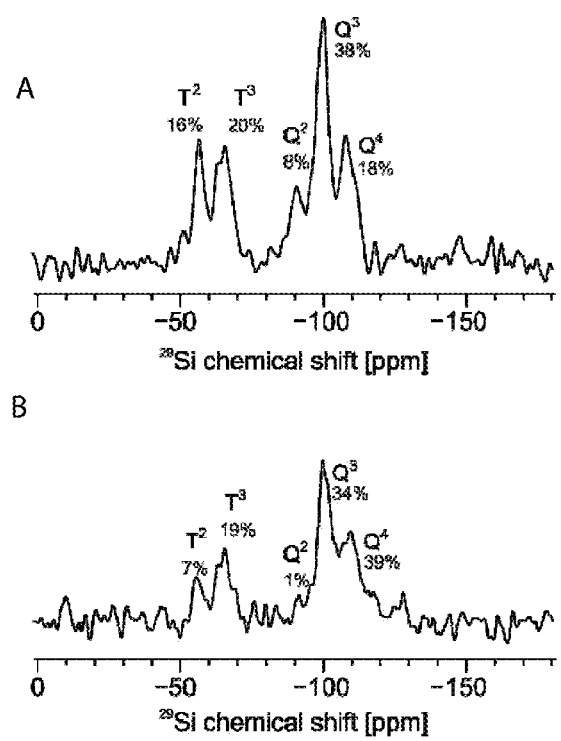

FIGS. 6A-B: Solid state SiMAS NMR of lyophilised silica capsules prepared from a) OTS and TEOS, b) DTS and TEOS. The molar ratio between two precursors was kept constant at 1:1.9.

Figure 7:
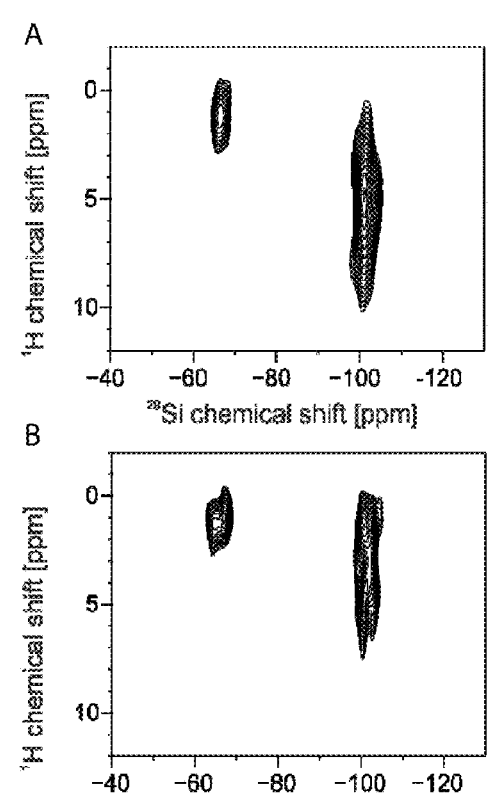

FIGS. 7A-B: $^{29}Si\{^1H\}$ CP-MAS correlation spectra of sample UPSI162 probing (a) closest spatial proximities and (b) larger distances on the nm length scale.

FIGS. 8A-C: SEM images from silica nanocapsules prepared with different molar ratios of OTS:TEOS, namely a) 1:5.6, b) 1:3.7 and c) 1:1.9.

FIGS. 9A-B: $^{13}$C-NMR of $D_2O$ hydrated thick shell of silica capsules containing GDH (OTS:TEOS was 1:1.9).

Figure 10:
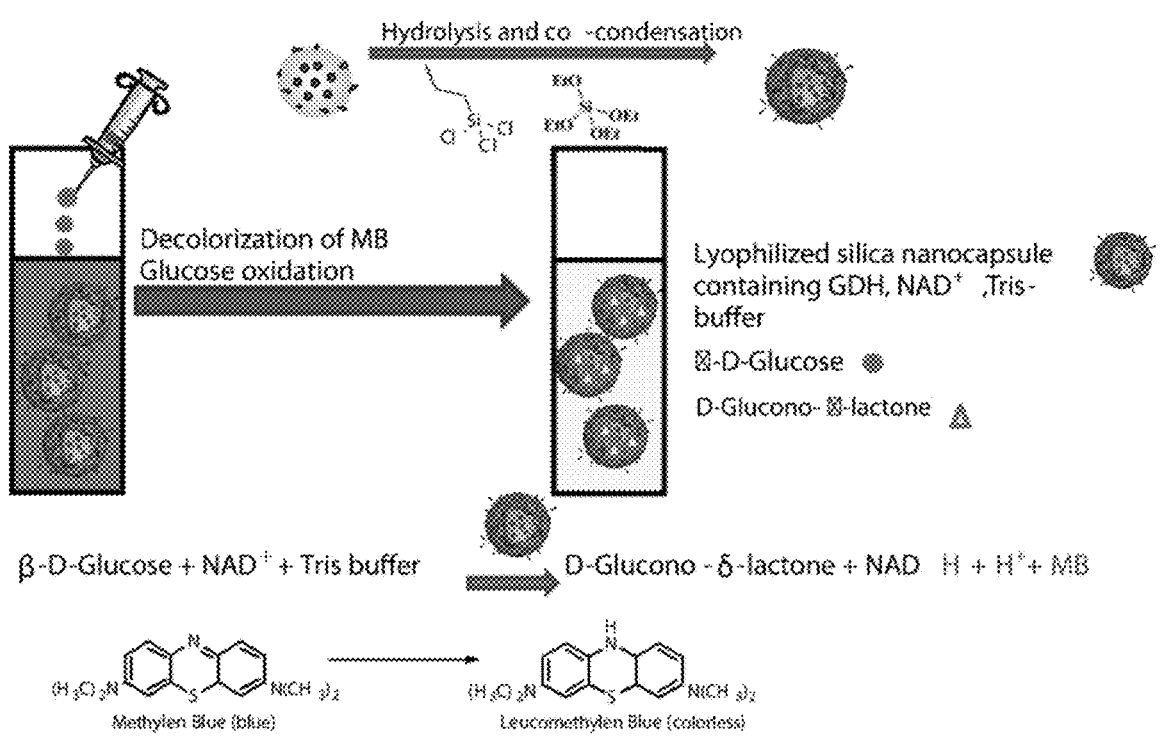

FIG. 10: Schematic depiction of the biocatalytic reaction between glucose and encapsulated GDH in the presence of methylene blue (MB).

Figure 11:
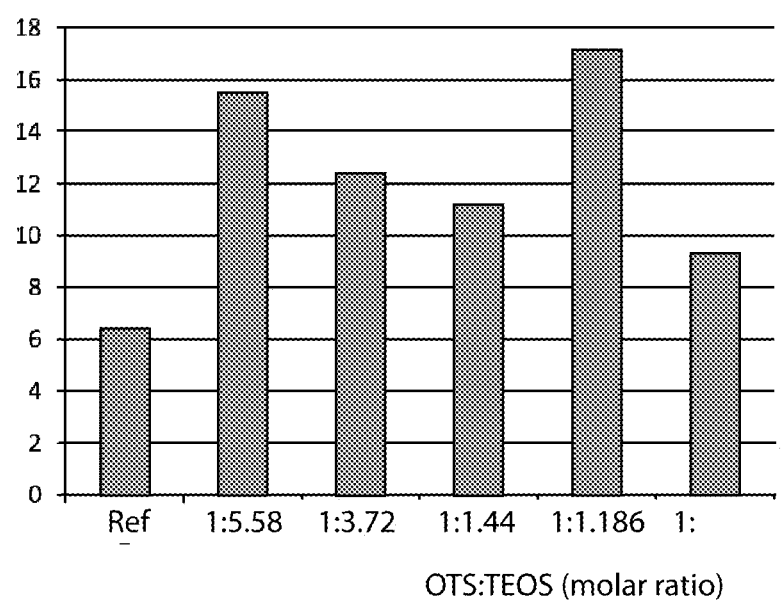

FIG. 11: Decolorisation time of methylene blue (MB) dependent on the molar ratio of OTS:TEOS.

Figure 12:
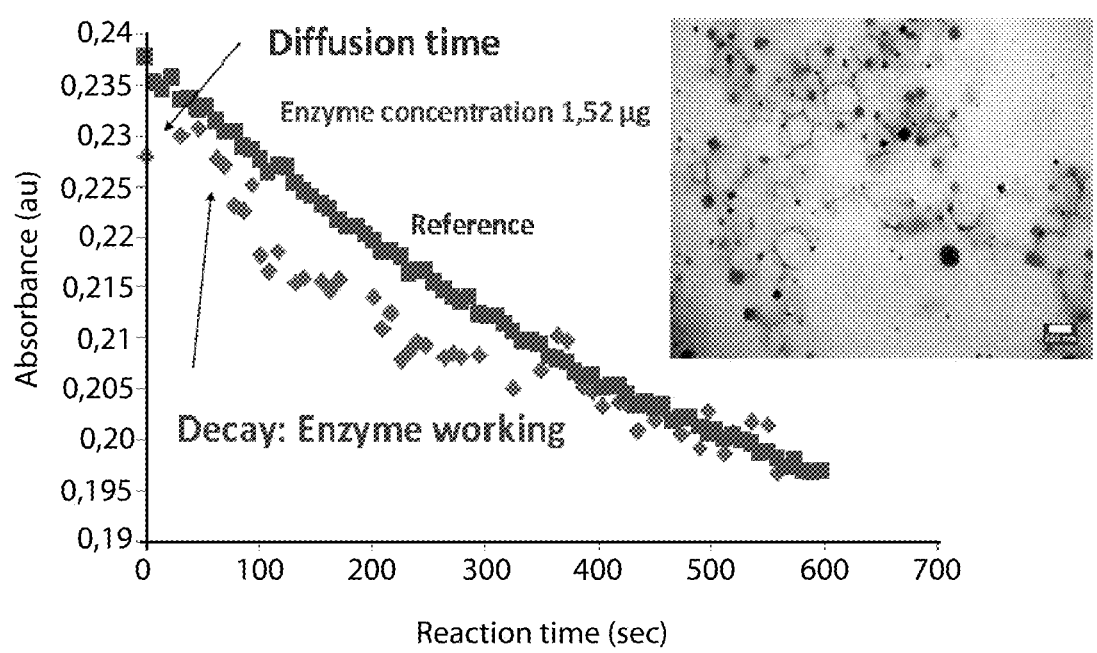

FIG. 12: Kinetic study of GDH activity in solution in the presence of silica nanocapsule (GDH is not encapsulated) with OTS/TEOS=1.1.9 and a GHD core concentration of 0.1 mg/ml.

Figure 13:
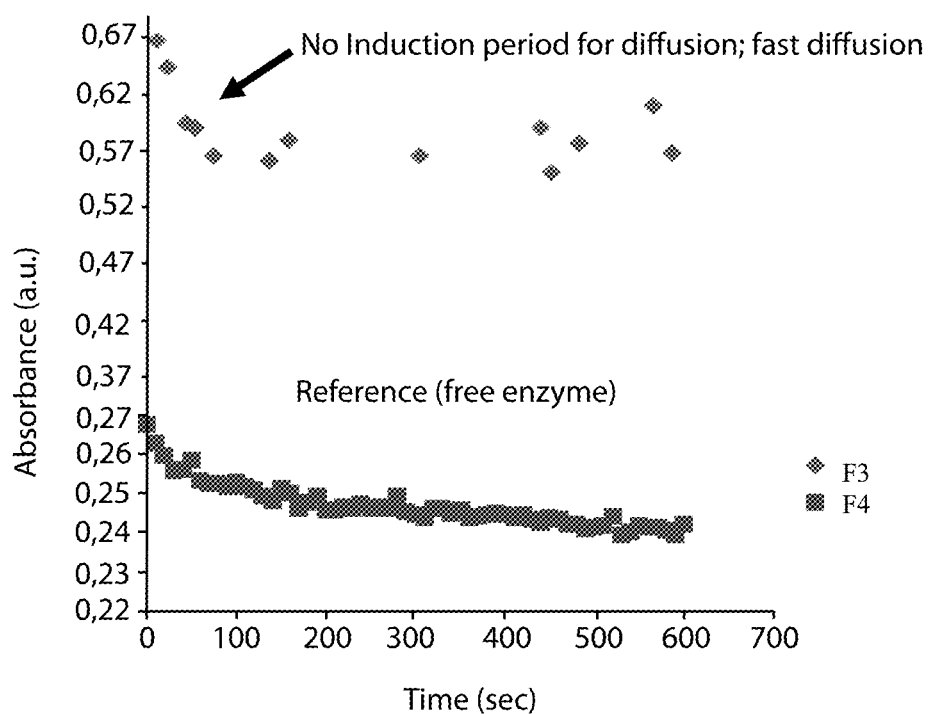

FIG. 13: Kinetic study of encapsulated GDH activity in silica nanocapsule with OTS/TEOS=1:1.9 and a GHD core concentration of 0.1 mg/ml.

Figure 14:
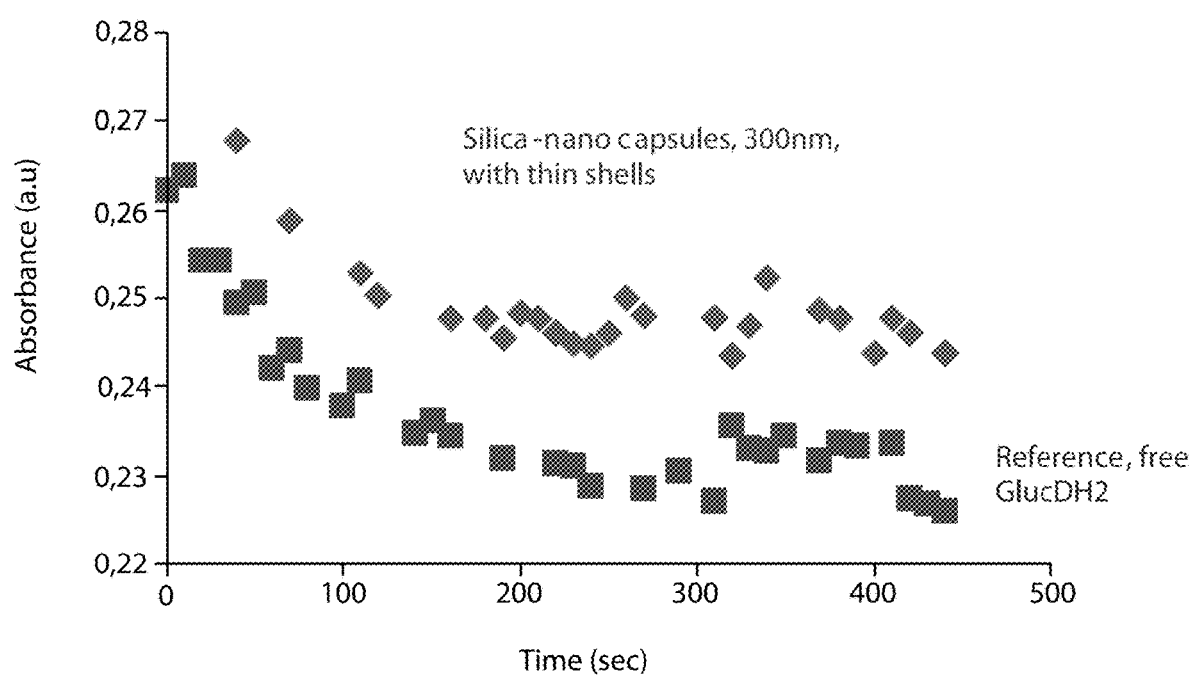

FIG. 14: Kinetic study of GDH activity for a silica nanocapsule with OTS/TEOS=1:1.9 and a GHD core concentration of 1 mg/ml.

Figure 15:
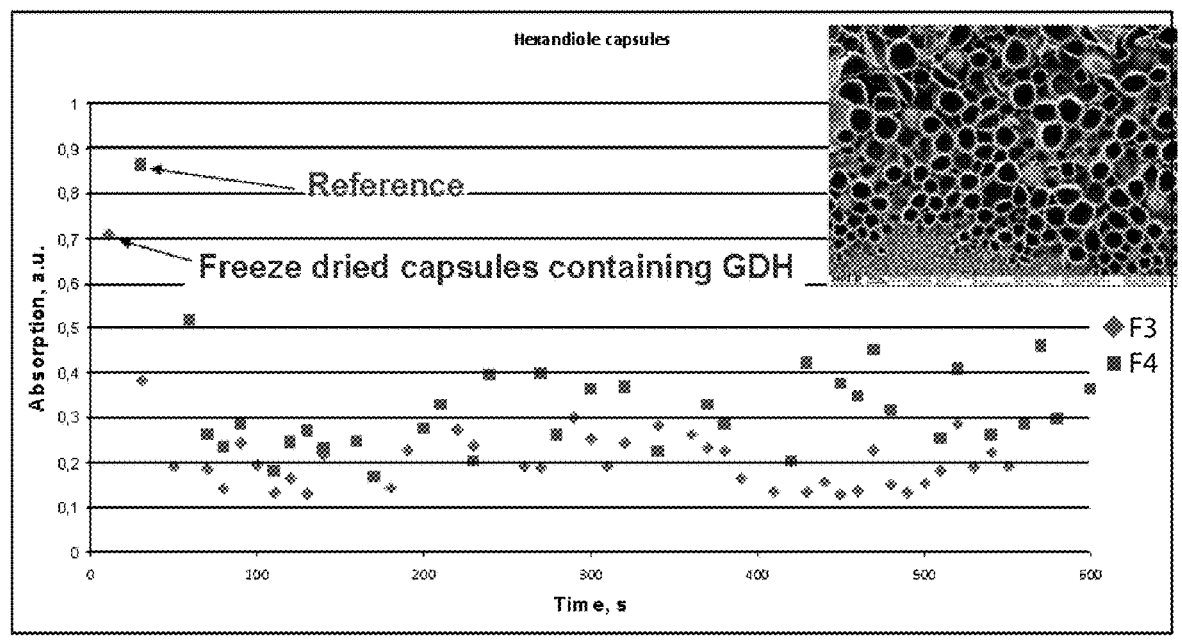

FIG. 15: Kinetic study of GDH activity for a silica nanocapsule from TDI and 1,6-hexanediol.

Figure 16A:
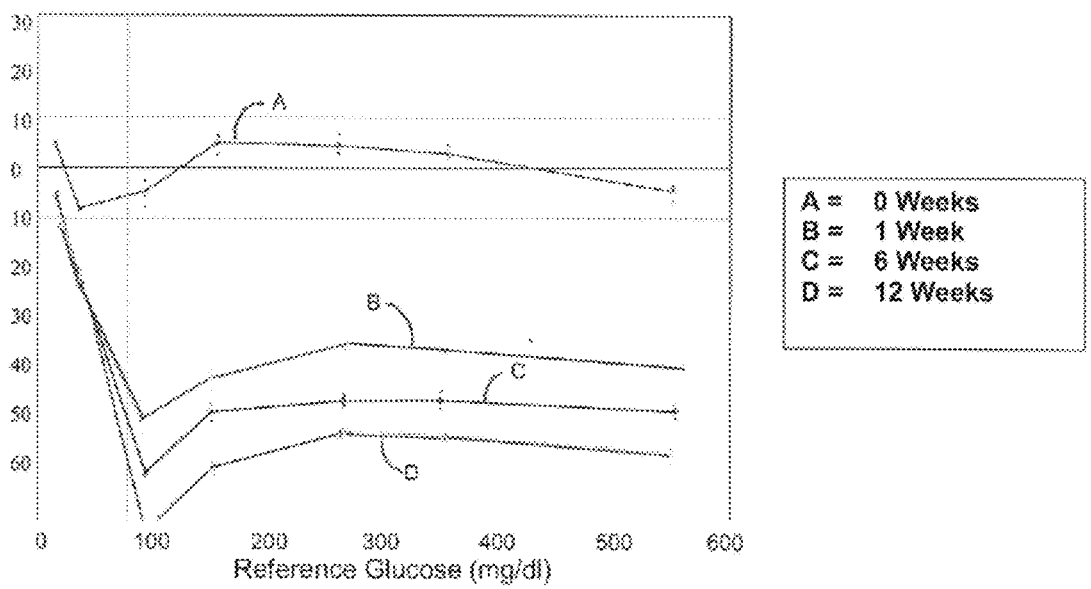
Figure 16B:
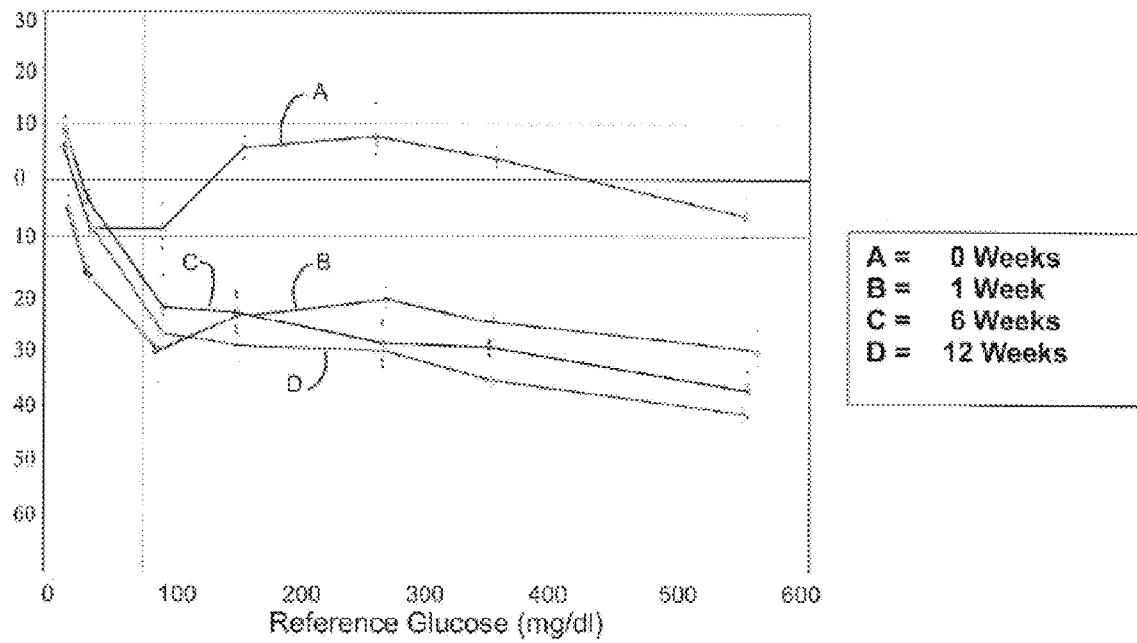

FIG. 16A and FIG. 16B: Activity of free GDH and encapsulated inside silica shell after 12 weeks incubation at 35° C.; 85% relative humidity. For FIG. 16A, the Y-axis is labeled as follows:

Lum Diff Ref (<=75'-' mg/dl, >75'/'%) Code (0.0-600.0 mg/dl) P Spectr(7), SavGol(21, ^2), lraw,-o/lpre0.1s, a-Dyn.1 (4.0 s,0.0 s, dl/l/dt>−1.0%/s), (base vector.6)), LMLog (xNrm wett.).

For FIG. 16B, the Y-axis is labeled as follows:

Lum Diff Ref (<=75'-' mg/dl, >75'/'%) Code (0.0-600.0 mg/dl) P Spectr(7), SavGol(21, ^2), lraw,-o/lpre0.1 s, a-Dyn.1 (4.0 s,0.0 s,dl/l/dt>−1.0%/s), (base vector.7)), LMLog (xNrm wett.).

Figure 17:
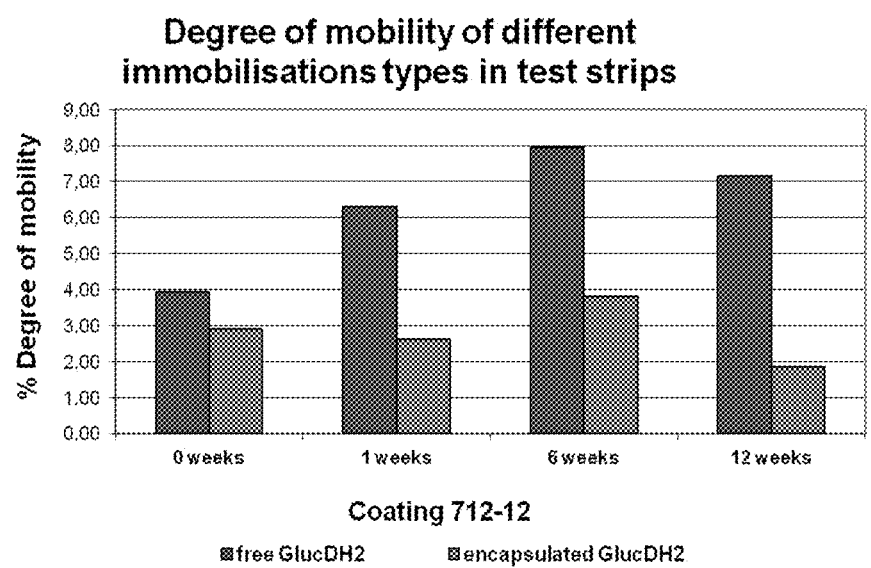

FIG. 17: Degree of mobility of free and encapsulated GDH in test strips. The obtained values for encapsulated GDH are lower compared to free GDH.

EXAMPLES

Materials

Glucose dehydrogenase (GDH), nicotinamide adenine dinucleotide (NAD$^+$), carbo-NAD$^+$, 2-amino-2(hydroxymethyl)1,3-propanediol (Tris) were provided from Roche, Germany. Sodium chloride (NaCl, analytical grade) and cyclohexane (HPLC) were supplied by VWR. Trichloro(octadecyl)silane (OTS, ≥90%) and tetraethoxysilane (TEOS, ≥99%) were purchased from Aldrich. Polyglycerol polyricinoleate (GRINDSTED® PGPR, Danisco A/S, Denmark) was applied as hydrophobic surfactant. Milli-Q water was used in all experiments. 1,6-hexanediol (Sigma Aldrich), 1,3-dihydroxyacetone (Acros), glycerol (Merck), poly(vinyl alcohol) (PVA) ($M_w$=25000 g·mol$^{-1}$, Polysciences Inc), lactic acid (Sigma Aldrich) and hyaluronic acid ($M_w$=140000 g·mol$^{-1}$, Fluka) were used as hydrophilic monomers for the polyurethane synthesis. The oil soluble block copolymer surfactant poly[(ethylene-co-butylene)-b-(ethylene oxide)], P(E/B-b-EO), consisting of a poly(ethylene-co-butylene) block ($M_w$=3700 g·mol$^{-1}$) and a poly(ethylene oxide) block ($M_w$=3600 g·mol$^{-1}$) was vacuum dried prior to use. The hydrophobic monomer toluene 2,4-diisocyanate (TDI, 98%) was purchased from Sigma Aldrich. Geropon®T77 was provided by ROCHE.

Characterization of Nanocapsules

The average size and the size distribution of the nanocapsules were measured by means of dynamic light scattering (DLS) with diluted dispersions (40 μl sample were diluted in 1 mL water) on a PSS Nicomp Particle Sizer 380 (Nicomp Particle Sizing Systems, USA) equipped with a detector at 90° scattering mode at 20° C.

Scanning electron microscopy (SEM) studies were done on a field emission microscope (LEO (Zeiss) 1530 Gemini, Oberkochen, Germany) working at an accelerating voltage of 170 V. Generally, the samples were prepared by diluting the capsule dispersion in cyclohexane or demineralized water (for redispersed samples) to about 0.01% solid content. Then one droplet of the sample was placed onto silica wafer and dried under ambient conditions over night. No additional contrast agent was applied. The solid content of the capsule dispersion was measured gravimetrically.

Example 1. Formation of Poly(Urethane/Urea) Nanocapsules with 1 mg/mL Enzyme (GDH)

Polyurethane nanocapsules were synthesized by a polyaddition reaction, whereas the reaction took place at the droplets' interface. The dispersed aqueous phase contained different monomers (see Table 1), which were mixed with 750 mg of enzyme solution. Enzyme solution was prepared as followed: 10 mg of GDH was dissolved in 1 mL of 0.1 M Tris buffer containing NaCl 0.2 M (pH 8.5) and incubated for 2 h at 4° C. The enzyme was diluted to 1 mg/mL with the diluting buffer (3.8 mM NAD$^+$ or carba-NAD$^+$ in Tris buffer).

The continuous oil phase contained the surfactant P(E/B-b-EO) (70 mg), which was dissolved in cyclohexane (6.0 g). Both phases were mixed together and the miniemulsion was obtained by ultrasonication. Ultrasonication procedure was applied for 3 min at 45% amplitude (20 s pulse, 10 s pause) using a Branson Sonifier W450-Digital under ice cooling in order to prevent evaporation of the solvent.

Figure 1:
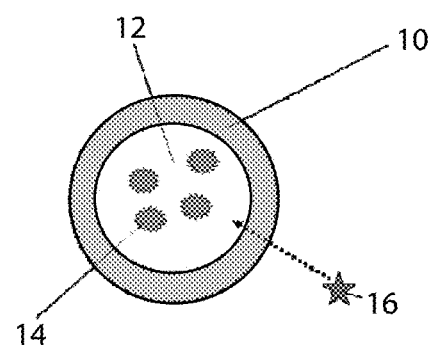
FIG. 1: Schematic depiction of a permeable nanocapsule, having incorporated an enzyme molecule according to the invention.
Figure 2:
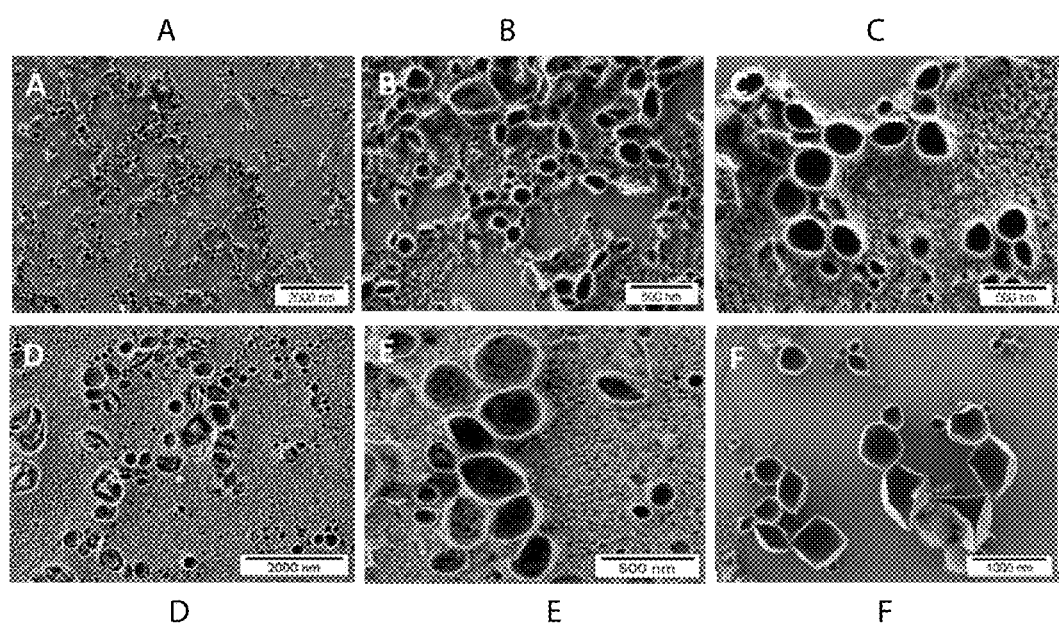

A clear solution consisting of cyclohexane (4 g), P(E/B-b-EO) (10 mg), and TDI (170 mg) was prepared and then added to the miniemulsion over 5 min at 25° C. The mixture was stirred for 24 h at 25° C. The size and size distribution was measured using dynamic light scattering (DLS), values see Table 1. The morphology was studied by scanning electron microscopy. The images are depicted in FIG. 1.

TABLE 1

Characterization of poly(urethane/urea) capsules obtained from different monomers. The monomer/TDI ratio was kept the same in runs from 1 to 4 as 1:1.5.

| Run | Monomer | Amount of monomer, mg | Diameter, nm/STD, % |
|---|---|---|---|
| 1 | 1,6-hexanediol | 76 | 230/26 |
| 2 | lactic acid | 68 | 280/28 |
| 3 | 1,3-dihydroxyacetone | 58 | 315/30 |
| 4 | glycerol | 140 | 295/30 |
| 5 | poly(vinyl alcohol) | 60 | 440/31 |
| 6 | hyaluronic acid | 30 | 360/30 |

Example 2. Formation of Poly(Urethane/Urea) Nanocapsules with 1, 0.1 and 0.01 m/mL of Enzyme (GDH)

Polyurethane nanocapsules were synthesized as described in Example 1. The dispersed aqueous phase contained different monomers (see Table 2), which were mixed with 750 mg of enzyme solution. Enzyme solution was prepared as followed: 10 mg of GDH was dissolved in 1 mL of 0.1 M Tris buffer containing NaCl 0.2 M (pH 8.5) and incubated for 2 h at 4° C. The enzyme was diluted to 1, 0.1 or 0.001 mg/mL with the diluting buffer (3.8 mM $NAD^+$ or carba-$NAD^+$ in Tris buffer).

The size and size distribution of the resulting capsules was measured using dynamic light scattering (DLS), values see Table 2.

TABLE 2

Characterization of poly(urethane/urea) capsules obtained from different monomers.
The monomer/TDI ratio was kept the same in runs from 1 to 4 as 1:1.5.

| Run | Monomer | Amount of monomer, mg | Diameter, nm/STD, % GDH concentration, mg per mL | | |
|---|---|---|---|---|---|
| | | | 1 | 0.1 | 0.001 |
| 1 | 1,6-hexanediol | 76 | 230/26 | 235/27 | 230/27 |
| 2 | lactic acid | 68 | 280/28 | 270/29 | 280/28 |
| 3 | 1,3-dihydroxyacetone | 58 | 315/30 | 325/30 | 360/31 |
| 4 | glycerol | 140 | 295/30 | 340/30 | 395/31 |
| 5 | poly(vinyl alcohol) | 60 | 440/31 | 475/31 | 525/33 |
| 6 | hyaluronic acid | 30 | 360/30 | 400/31 | 420/30 |

Example 3. Formation of Polyurethane Nanocapsules with 100, 200, 300 and 500 mg/mL of Enzyme (GDH)

Polyurethane nanocapsules were synthesized as described in Example 1. The dispersed aqueous phase contained a monomer, 1,6-hexanediol, (76 mg) and 750 mg of enzyme solution (100, 200, 300 or 500 mg/mL). Enzyme solution was prepared as followed: 100, 200, 300 or 500 mg of GDH was dissolved in 1 mL of 0.1 M Tris buffer containing NaCl 0.2 M (pH 8.5) and incubated for 2 h at 4° C.

The average size, size distribution and the enzyme activity of the obtained capsules are summarized in Table 3.

TABLE 3

Characterization of poly(urethane/urea) capsules obtained from 1,6-hexanediol and TDI.

| Sample | Concentration of GDH solution for capsules preparation (mg/mL) | Diameter, nm/STD, % | GDH activity (KU/g lyophilised capsules) |
|---|---|---|---|
| UPGDH1 | 100 | 202/43 | 14.7 |
| UPGDH2 | 200 | 310/31 | 20.3 |
| UPGDH3 | 300 | 200/42 | 30.1 |
| UPGDH4 | 500 | 120/43 | 45.5 |

Example 4. Formation of Silica Nanocapsules with 1 and 0.1 mg/mL of Enzyme (GDH)

A heterophase mixture comprising 0.65 g of enzyme solution (1 or 0.1 mg/mL) as a dispersed phase and 6.25 g of cyclohexane containing 55 mg of the hydrophobic surfactant PGPR as a continuous phase was prepared. Enzyme solution was prepared as followed: 10 mg of GDH was dissolved in 1 mL of 0.1 M Tris buffer containing NaCl 0.2 M (pH 8.5) and incubated for 2 h at 4° C. The enzyme was diluted to 1 or 0.1 mg/mL with the diluting buffer (3.8 mM $NAD^+$ or carba-$NAD^+$ in Tris buffer).

The inverse miniemulsion was obtained by ultrasonication of the mixture at 45% amplitude (20 s pulse and 10 s pause) for 3 min under an ice cooling. A known amount of OTS/TEOS mixture (1:1.9 molar ratio) and 10 mg of PGPR dissolved in 2 g of cyclohexane were added drop-wise into the miniemulsion. The hydrolysis and co-condensation of the silane mixture took place at the droplets interface with subsequent formation of the silica shell. The reaction was carried out at room temperature overnight.

A schematic depiction of capsule synthesis and subsequent redispersion in an aqueous phase is shown in FIGS. 3A and 3B. A SEM image of silica nanocapsules including a schematic depiction of the shell structure is shown in FIG. 3C.

Example 5. Formation of Silica Nanocapsules with 300 mg/mL of Enzyme (GDH) (Sample UPSI178)

Silica nanocapsules with 300 ng/mL GDH were prepared substantially as described in Example 4. Enzyme solution was prepared as follows: 300 mg of GDH were dissolved in 1 mL of PBS buffer (pH 8.5) and the solution was incubated for 2 h at 4° C.

The inverse miniemulsion was obtained by ultrasonication of the mixture at 45% amplitude (20 s pulse and 10 s pause) for 3 min under an ice cooling. A known amount of OTS/TEOS mixture (1:1.9 molar ratio) and 10 mg of PGPR dissolved in 2 g of cyclohexane were added drop-wise into the miniemulsion. The hydrolysis and co-condensation of the silane mixture took place at the droplets interface with subsequent formation of the silica shell. The reaction was carried out at room temperature overnight.

Figure 4:
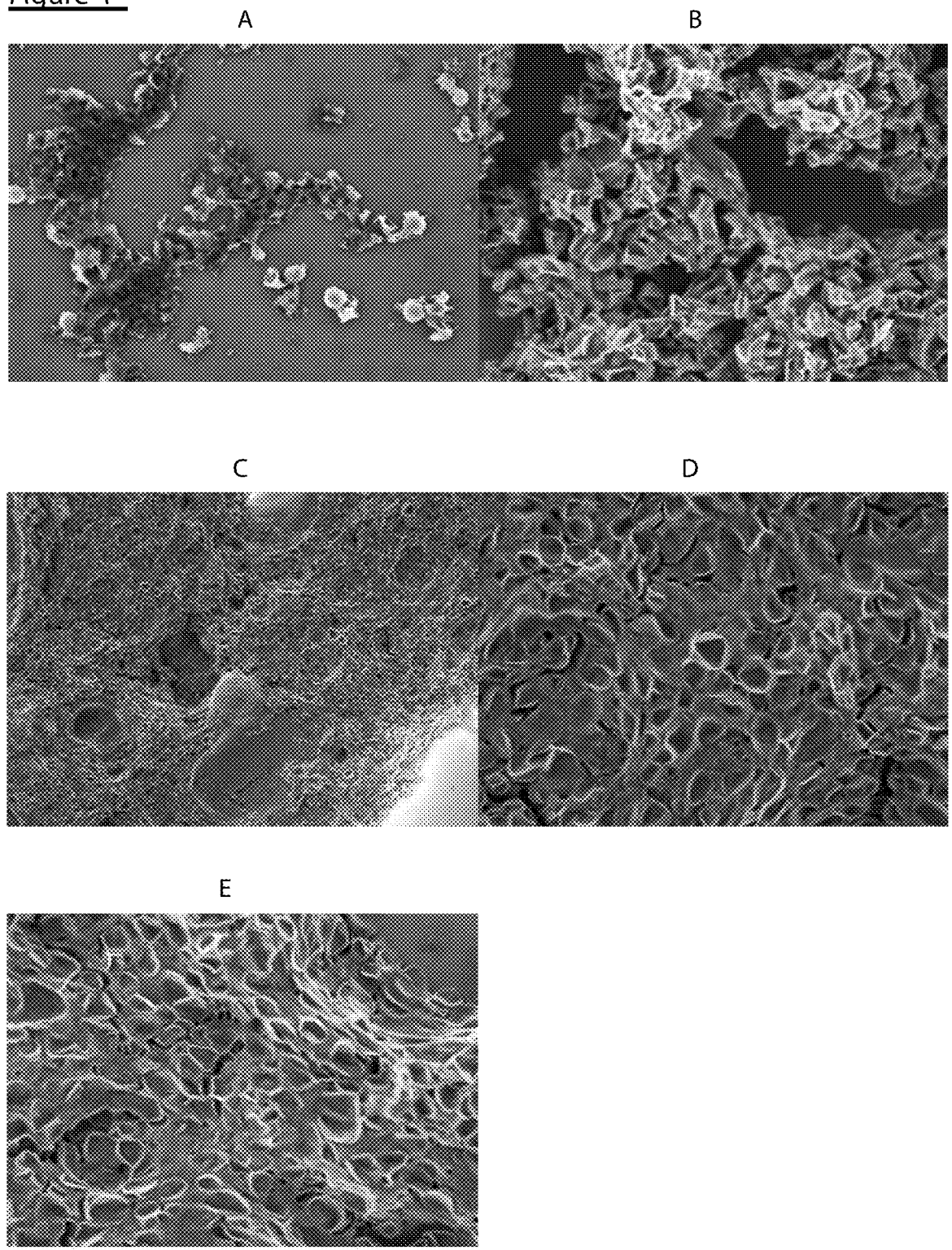

The obtained nanocapsules in the cyclohexane phase were two times centrifuged at 2000 rpm for 20 min to remove the oil-soluble surfactant (PGPR) from the suspension. The washed nanocapsules were redispersed in 0.5 wt % Geropon®T77 solution and afterwards freeze-dried. The lyophilised nanocapsules were purified by repetitive centrifugation in water to separate not-encapsulated enzyme from the sample. The washed capsules were redispersed in 0.5 wt % Geropon®T77 before being freeze-dried again and stored as a powder until the use. The morphology was studied by scanning electron microscopy. The images are shown in FIG. 4.

The inorganic content of 10.1 wt % with respect to all ingredients (from the cyclohexane phase) was determined by thermogravimetric analysis (TGA).

Example 6. Formation of Silica Nanocapsules with Different Molar Ratios of OTS:TEOS and 1 mg/mL of Enzyme (GDH)

Silica nanocapsules with different molar ratios of OTS:TEOS were prepared.

An inverse miniemulsion was obtained as described in Example 4. Different mixtures of OTS/TEOS (see Table 4) and 10 mg of PGPR dissolved in 2 g of cyclohexane were added drop-wise into the miniemulsion. The hydrolysis and co-condensation of the silane mixture took place at the droplets interface with subsequent formation of the silica shell. The reaction was carried out at room temperature overnight.

TABLE 4

Characterization of silica capsules obtained with different molar ratio of silica precursors (OTS:TEOS).

| Samples | OTS:TEOS (molar ratio) | Average particle size (nm) | $R_w$ | Inorganic content (%) Theoretical values | TGA at 900° C. |
|---|---|---|---|---|---|
| UPSI122 | 1:5.6 | 225 | 37 | 29 | 16 |
| UPSI123 | 1:3.7 | 225 | 52 | 28 | 25 |
| UPSI124 | 1:1.9 (30 µL) | 256 | 89 | 27 | 24 |
| UPSI125 | 1:1.9 (60 µL) | 294 | 51 | 41 | 20 |

Example 7. Silica Nanocapsules with Different Alkyl Chain Length of Alkyltrichlorosilane (Molar Ratio of $RSiCl_3$ to TEOS Was Fixed at 1:1.86) and 1 mg/mL of Enzyme (GDH)

Silica nanocapsules with different alkyltrichlorosilanes, i.e. octadecyltrichlorosilane (OTS), dodecyltrichlorosilane (DTS) and hexyltrichlorosilane (HTS) were prepared.

An inverse miniemulsion was obtained as described in Example 4. A known amount of $RSiCl_3$/TEOS mixture (see Table 5) (molar ratio of $RSiCl_3$ to TEOS was fixed at 1:1.9) and 10 mg of PGPR dissolved in 2 g of cyclohexane were added drop-wise into the miniemulsion. The hydrolysis and co-condensation of the silane mixture took place at the droplets interface with subsequent formation of the silica shell. The reaction was preceded at room temperature overnight.

TABLE 5

Characterization of silica capsules obtained with different alkyl chain length of alkyltrichlorosilane ($RSiCl_3$).

| Sample | Alkyl chain length of $RSiCl_3$ | Average particle size (nm) | Inorganic content (%) Theoretical calculation | TGA at 900° C. |
|---|---|---|---|---|
| USPI141 | $C_{18}H_{27}$ (OTS) | 225 | 29 | 26 |
| UPSI162 | $C_{12}H_{25}$ (DTS) | 222 | 33 | 14 |
| UPSI163 | $C_6H_{13}$ (HTS) | 222 | 36 | 11 |

Example 8. Characterization of Silica Nanocapsules Containing GDH

FTIR was employed to characterize the chemical composition of the silica capsules (FIG. 5). The peaks at 3450 cm$^{-1}$ and at 940 cm$^{-1}$ correspond to hydrogen bonded —OH stretching of silanol group and of Si—OH stretching, respectively. A high intensity band localized at 1064 cm$^{-1}$ is attributed to Si—O—Si stretching with a shoulder at 1150 cm$^{-1}$ from Si—C stretching (alkylsilane moiety). The peaks centred at 2850 and 2900 cm$^{-1}$ correspond to CH stretching of alkyl moieties. The small peak at 815 cm$^{-1}$ appears to be asymmetric flexion of the Si—O. The presence of encapsulated enzyme (GDH) in the samples could be confirmed by the presence of peaks at 3250, 1602 and 1722 cm$^{-1}$ which are characteristic for —NH and amide stretching.

$^{29}$Si MAS NMR in the solid state has been used to determine the degree of condensation and the local structure in terms of $Q^{(n)}$ and $T^{(n)}$ sites of the obtained silica material. To obtain quantitative results for the different $Q^{(n)}$ and $T^{(n)}$ sites in the materials, direct excitation spectra and MAS conditions have been recorded with a small excitation angle (~20°), 15 s relaxation delays and high power $^1$H decoupling. The results are listed in Table 6. Remarkably, the higher yield obtained for the trichloro silanes with longer alkyl chains does not lead to a better degree of condensation of the silica network, which would be reflected in a higher content of higher order Q groups, as the ideal silica network would consist of $Q^{(4)}$ groups only. In fact, the condensation in sample UPSI162 seems to be more complete compared to that of UPSI141. The $^{29}$Si{$^1$H} CP-MAS correlation spectrum shown in FIG. 6 demonstrates that the aliphatic protons of the organic substituent of $T^{(n)}$ groups in the material correlate only with the $^{29}$Si NMR signals around −60 ppm, assigned to T groups, which $Q^{(3)}$ groups at −100 ppm correlate with a very broad OH proton signal centred around 5 ppm in the proton dimension. When a spin diffusion delay is introduced in the correlation experiment, correlations on larger length scales can be probed.

TABLE 6

Results of solid state $^{29}$Si MAS NMR analysis.

| Sample | Alkyl chain length of $RSiCl_3$ | Average diameter (nm) | Silica structure: Ratio of silaxane units (%) | | | | |
|---|---|---|---|---|---|---|---|
| | | | $T^2$ | $T^3$ | $Q^2$ | $Q^3$ | $Q^4$ |
| UPSI124 | $C_{18}H_{37}$ (OTS) | 225 | 16 | 20 | 8 | 38 | 18 |
| UPSI162 | $C_{12}H_{26}$ (DTS) | 222 | 7 | 19 | 1 | 34 | 39 |

$Q^n$: $(Si(OSi)_n(OH)_{4-n}$ (n=0-4); $T^n$: $(R(OSi)_n(OH)_{3-n}$ (n=0-3)

The spectrum shown in FIG. 7b has been recorded with a diffusion delay of 10 ms, which corresponds to distances below 1 nm in a relatively dilute proton spin bath like our silica material. However a well-defined distance is very difficult to estimate, due to the heterogeneities of the $^1$H spin with a high $^1$H density at the aliphatic chains of the TH groups and a low $^1$H density at the $Q^{(n)}$ sites, which experimentally leads to the finding that $^1$H polarization diffuses from the $T^{(n)}$ groups to the $Q^{(n)}$ but the polarization of the OH groups at $Q^{(2)}$ and $Q^{(3)}$ sites cannot be observed at $T^{(n)}$ sites. This experiment clearly demonstrates that $T^{(n)}$ and $Q^{(n)}$ sites are in close spatial proximity in the silica material and in particular from the missing correlation signal between aliphatic protons and $Q^{(n)}$ sites in FIG. 7a any incorporation of surfactant into the silica material can be excluded.

Figure 8:
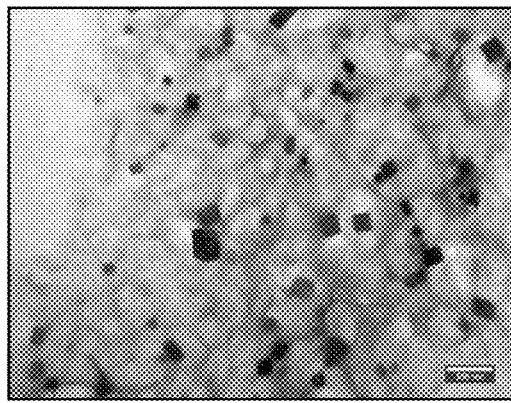
Figure 8:
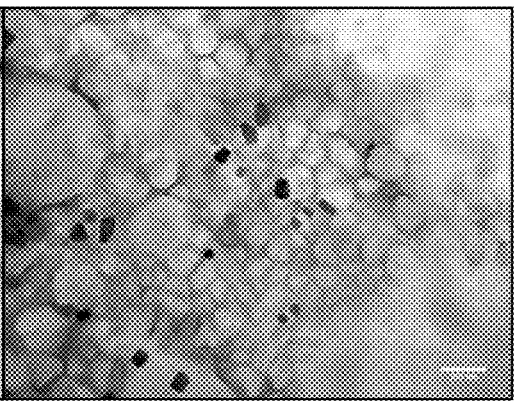
Figure 8:
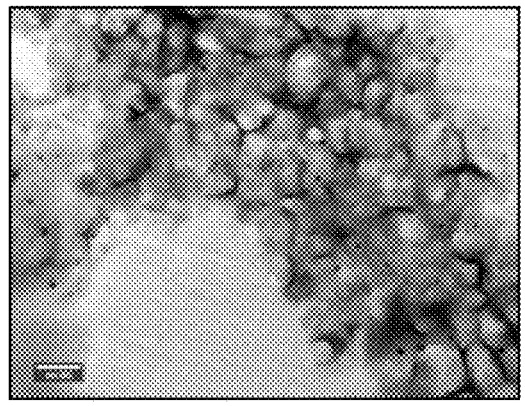

An increasing molar ratio of alkyltrichlorosilane, e.g. OTS to tetraalkoxysilane, e.g. TEOS gave an increased shell thickness as shown in FIG. 8.

Example 9. Biocatalytic Properties of Encapsulated GDH

The crucial factors, which determine the biocatalytic properties of the encapsulated GDH are related to the diffusion limitation of glucose through the shell and enzyme stability.

Figure 9:
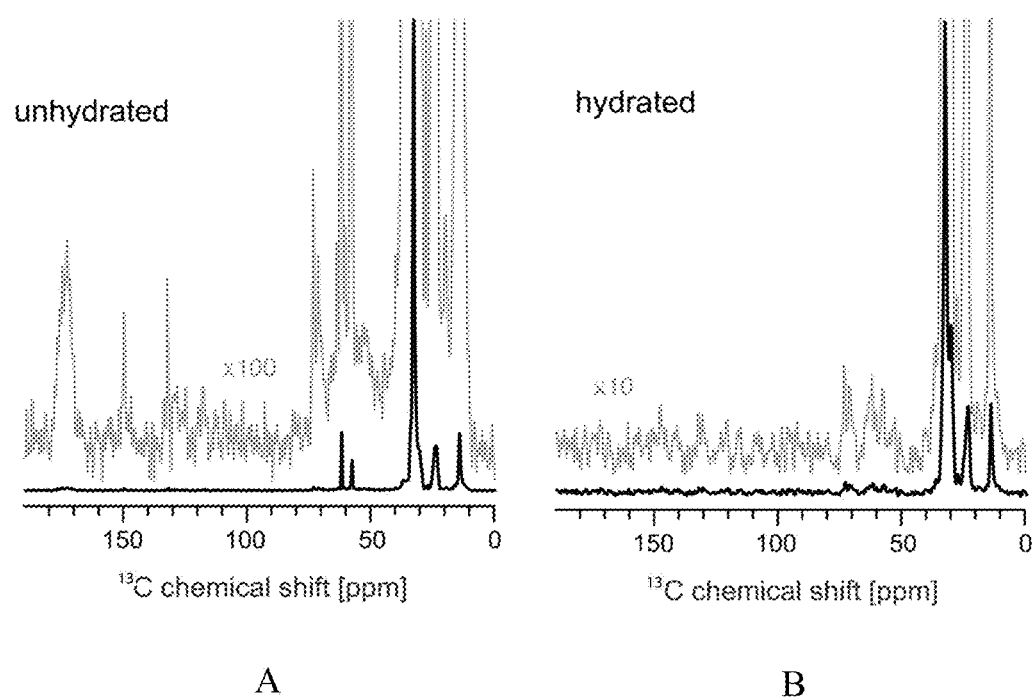

The enzyme mobility in silica capsules was investigated by $^{13}$C CP-MAS NMR. The presence of the Tris buffer and GDH was confirmed by the peaks at 60 and 65 ppm denoted as C—O and 170 ppm attributed to carbonyl groups. The overall decrease of the signal intensity in the CP-MAS spectrum of the hydrated sample, and in particular the vanishing of the carbonyl signal due to the higher molecular mobility in the hydrated state was clearly observed (FIG. 9). This could be a strong evident to mention that the enzyme is trapped in the dried capsules, which could be hydrated to enable enzyme to mobile in the small confinement.

The enzymatic activity of GDH encapsulated in silica nanocapsules was determined by the colorimetric analysis based on a reduction of methylene blue (MB) in the presence of NADH (Yudkin, Biochem. J. 28 (1934), 1454) which is produced during the glucose oxidation (FIG. 10). The reactions are triggered when the glucose molecules are able to diffuse inside the capsules containing GDH.

According to the obtained data all nanocapsules showed enzymatic activity. The decolorization time for all studied capsules was higher than that for the reference sample (silica capsules physically mixed with free GDH solution), indicating that the size of the pores is smaller than the size of the enzyme (which is 4.1 nm in radius determined from DLS). It could be also seen that the decolorization time is lower (the permeability is faster) for the silica capsules having less shell material. After encapsulation, the enzyme GDH still remains active, having about 70% of the initial activity.

The decolorisation time was dependent from the molar ratio of the alkyltrichlorosilane (e.g. OTS) to TEOS as shown in FIG. 11.

In FIG. 12 a kinetic study of the GDH activity measured by methylene blue decolorisation for a silica nanocapsule having a 15 nm thick shell (OTS/TEOS=1/1.9) and a core GDH concentration of 0.1 mg/ml is shown. The decolorisation rate for the reference sample (free enzyme) was as fast as the decolorisation rate with encapsulated enzyme. The observed time difference was based on a delay for the encapsulated enzymes caused by the time required for a diffusion of glucose through the capsule shell (diffusion time).

In FIG. 13 a kinetic study for a thin shell nanocapsule (molar ratio OTS:TEOS=1.9) with a core GDH concentration of 0.1 mg/ml is shown. In this case, no delay is found, i.e. a rapid diffusion through the thin shell takes place.

When increasing the enzyme concentration, the reaction rate increases as shown in FIG. 14 for a thin shell silica nanocapsule (molar ratio OTS:TEOS=1:1.9) and a GDH concentration in the core of 1 mg/ml.

A kinetic study of the enzymatic reaction in polyurethane capsules (comonomer 1,6-hexanediol) is shown in FIG. 15. After freeze-drying and resuspending, the capsules had the same response time as the reference, i.e. unencapsulated GDH.

Example 10. Stability, Activity and Mobility Test for Enzyme Activity in Dry Layer Chemistry To show the application of GDH containing silica nanocapsules as glucose biosensors, the stability, activity and mobility tests in dry layer films were performed. The capsules containing 300 mg/ml GDH were synthesized for these studies using a molar ratio of OTS:TEOS of 1:1.9. The average particle size was 275±46 nm, the silica content was 13.8% and the specific activity 22 KU/g.

Test strips were manufactured comprising a first enzyme layer with either free GDH (280 KU/m$^2$) or encapsulated GDH (86 KU/m$^2$) and a second coating layer. The resulting test strips were incubated at 35° C. and 85% relative humidity. After 1, 6 and 12 weeks the total activity was determined. As can be seen in FIG. 16, the encapsulated enzyme shows higher stability in total activity than free GDH. Whereas free GDH shows 50-60% deviation after 6 weeks, the encapsulated GDH only shows 20-30% deviation. Thus, the encapsulated enzyme has a significantly higher functional stability than free enzyme, particularly when stored under warm and humid conditions.

For the elution of enzyme the test strip was treated for 10 minutes with ultrasound on ice in Tris buffer (0.1 M Tris; 0.2 M NaCl; 0.1% (w/v) albumin at pH 8.5). The activity was measured in the same Tris buffer system and the working solution in the cuvette contained additional 0.142 M glucose and 1.2 mM NAD. The absorption of the product NADH was detected at 340 nm in a spectrophotometer and the activity was calculated using the extinction coefficient of 6.3 [l mmol$^{-1}$ cm$^{-1}$]. The obtained data reveal the activity of 22.9 KU/capsule, which corresponds to 86 KU/m$^2$. For comparison, the activity of free GDH was 280 KU/m$^2$.

To characterize the enzyme mobility in the layer, the activity of supernatant obtained after washing the test strip was analyzed. The degree of mobility was defined as the activity of the supernatant in comparison to the total activity (FIG. 17).

CONCLUSION

The synthesis of silica nanocapsules with the average diameter of preferably 200-350 nm and containing active nicotinamide adenine dinucleotide (NAD$^+$/NADH) dependent GDH inside the aqueous core was achieved in a single-step inverse miniemulsion process by controlling restricted interfacial hydrolysis and co-condensation of silica precursors. The properties of the encapsulated GDH in silica capsules in terms of encapsulation efficiency, wettability, and mobility of the enzyme in the silica capsules of the enzyme has been investigated. The permeability of the silica shell enables the enzyme to be wet and mobile in the hydrated state. In addition, the encapsulated enzyme shows high activity and similar to free enzyme stability in dry layer strip tests. This engineered silica capsules provide a new horizon for the developing of glucose sensitive biosensors.

Polyurethane/urea nanocapsules with encapsulated GDH were also investigated. The enzyme encapsulated therein shows high activity and thus is suitable for application to diagnostic test strips.

The invention claimed is:

1. A diagnostic test element for the detection of an analyte comprising:
    an enzyme; and
    a silica nanocapsule substantially impermeable for the enzyme but permeable for an enzyme substrate, the enzyme being incorporated within the interior of the silica nanocapsule, the interior of the silica nanocapsule being free from a hydrophilic polymer,
    wherein the silica nanocapsule comprises a polyaddition and/or polycondensation product of monomers formed at the interface in a water-in-oil miniemulsion comprising a continuous oil phase and a discontinuous aqueous phase dispersed therein, the enzyme being present in the aqueous phase, and
    wherein the silica nanocapsule is a polycondensation product of a tetra-alkoxy silane with a compound RSiX$_3$,
        wherein X is halo and
        R is an optionally substituted C$_3$-C$_{30}$alkyl group.

2. The diagnostic test element of claim 1 wherein the halo is chloro.

3. The diagnostic test element of claim 1 wherein the silica nanocapsule has pores with a maximum size which is smaller than the size of the enzyme.

4. The diagnostic test element of claim 1 wherein the interior of the silica nanocapsule is also free from a structuring surfactant.

5. The diagnostic test element of claim 4 wherein the halo is chloro.

6. The diagnostic test element of claim 4 wherein the silica nanocapsule has pores with a maximum size which is smaller than the size of the enzyme.

7. A method for detecting an analyte by an enzymatic reaction, comprising:
providing a sample to be analyzed;
contacting the sample with the test element of claim 1; and
detecting an enzymatic reaction between the enzyme and the enzyme substrate.

8. A method for detecting an analyte by an enzymatic reaction, comprising:
providing a sample to be analyzed;
contacting the sample with the test element of claim 4; and
detecting an enzymatic reaction between the enzyme and the enzyme substrate.

9. A diagnostic test element for the detection of an analyte comprising:
an enzyme; and
a silica nanocapsule being substantially impermeable for the enzyme but permeable for an enzyme substrate, the enzyme being incorporated within the interior of the silica nanocapsule, the interior of the silica nanocapsule being free from a structuring surfactant,
wherein the silica nanocapsule comprises a polyaddition and/or polycondensation product of monomers formed at the interface in a water-in-oil miniemulsion comprising a continuous oil phase and a discontinuous aqueous phase dispersed therein, the enzyme being present in the aqueous phase, and
wherein the silica nanocapsule is a polycondensation product of a tetra-alkoxy silane with a compound $RSiX_3$,
wherein X is halo and
R is an optionally substituted $C_3$-$C_{30}$ alkyl group.

10. The diagnostic test element of claim 9 wherein the silica nanocapsule has pores with a maximum size which is smaller than the size of the enzyme.

11. The diagnostic test element of claim 9 wherein the halo is chloro.

12. A method for detecting an analyte by an enzymatic reaction, comprising the steps:
providing a sample to be analyzed;
contacting the sample with the test element of claim 9; and
detecting an enzymatic reaction between the enzyme and the enzyme substrate.

* * * * *